US009326846B2

(12) United States Patent
Devita Gerardi et al.

(10) Patent No.: US 9,326,846 B2
(45) Date of Patent: May 3, 2016

(54) ACCOMMODATING INTRAOCULAR LENS

(71) Applicant: NOVARTIS AG, Basel (CH)

(72) Inventors: Lauren Devita Gerardi, Des Plaines, IL (US); Kevin M. Lewellen, Arlington, TX (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/526,893

(22) Filed: Oct. 29, 2014

(65) Prior Publication Data

US 2015/0173891 A1 Jun. 25, 2015

Related U.S. Application Data

(60) Provisional application No. 61/918,942, filed on Dec. 20, 2013.

(51) Int. Cl.
*A61F 2/16* (2006.01)

(52) U.S. Cl.
CPC .......... *A61F 2/1648* (2013.01); *A61F 2/1635* (2013.01); *A61F 2002/1681* (2013.01)

(58) Field of Classification Search
CPC ... A61F 2/1624; A61F 2/1635; A61F 2/1648; A61F 2002/169–2002/16902; A61F 2250/0008; A61F 2250/0013; A61F 2250/0009; A61F 2250/0015; A61F 2250/0018; A61F 2250/0029; A61F 2250/0034; A61F 2250/0036; A61F 2250/0053; A61F 2250/0058; A61F 2250/0065; A61F 2250/0091
USPC .................. 623/6.37, 6.13, 6.22, 6.32, 6.34, 623/6.38–6.42, 6.52
See application file for complete search history.

(56) References Cited

U.S. PATENT DOCUMENTS

| | | | | |
|---|---|---|---|---|
| 4,434,515 A | * | 3/1984 | Poler | A61F 2/16 623/6.41 |
| 4,585,457 A | * | 4/1986 | Kalb | A61F 2/1616 623/6.13 |
| 4,932,966 A | | 6/1990 | Christie et al. | |
| 2003/0105522 A1 | * | 6/2003 | Glazier | A61F 2/1613 623/6.13 |
| 2005/0137703 A1 | * | 6/2005 | Chen | A61F 2/1629 623/6.13 |
| 2006/0100701 A1 | * | 5/2006 | Esch | A61F 2/1613 623/6.13 |
| 2007/0203578 A1 | | 8/2007 | Scholl et al. | |
| 2008/0021550 A1 | * | 1/2008 | Richardson | A61F 2/1629 623/6.37 |
| 2009/0157179 A1 | * | 6/2009 | Pinto | A61F 2/16 623/6.11 |
| 2009/0171458 A1 | * | 7/2009 | Kellan | A61F 2/1629 623/6.46 |

(Continued)

FOREIGN PATENT DOCUMENTS

WO  WO2014049185 A1 * 4/2014 .......... A61F 2/16015

OTHER PUBLICATIONS

PCT/US2014/062810; International Search Report; International Searching Authority, Jan. 29, 2015, 2 pgs.

*Primary Examiner* — Paul Prebilic

(74) *Attorney, Agent, or Firm* — Jason Finch

(57) ABSTRACT

An accommodating intraocular lens includes an optic and four haptics. the optic includes an outer wall, a solid posterior optic, an anterior fluid chamber, an anterior membrane and a fluid reservoir within the outer wall surrounding the anterior fluid chamber and the solid posterior optics. The four haptics are attached to the outer wall at four attachment points. Each of the four haptics includes an arc member extending between successive attachment points and contacting the outer wall only at the attachment points. Each of the arc members is configured to compress laterally under accommodative forces.

4 Claims, 1 Drawing Sheet

(56) References Cited

U.S. PATENT DOCUMENTS

| | | |
|---|---|---|
| 2010/0094412 A1 | 4/2010 | Wensrich et al. |
| 2010/0324671 A1 | 12/2010 | Shadduck |
| 2010/0324672 A1* | 12/2010 | Esch ............... A61F 2/1613 623/6.13 |
| 2011/0118834 A1 | 5/2011 | Lo et al. |
| 2012/0059465 A1* | 3/2012 | Brady ................ A61F 2/14 623/6.39 |
| 2014/0180405 A1 | 6/2014 | Weinschenk, III et al. |
| 2015/0366660 A1* | 12/2015 | Fernandez Martinez et al. ............ A61F 2/1635 623/6.13 |

* cited by examiner

ACCOMMODATING INTRAOCULAR LENS

This application claims the priority of U.S. Provisional Application No. 61/918,942 filed Dec. 20, 2013.

TECHNICAL FIELD

This invention relates generally to the field of accommodating intraocular lenses and, more particularly, to a haptic design for a curvature changing accommodating intraocular lens.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and ultrasonically vibrated. The vibrating cutting tip liquefies or emulsifies the lens so that the lens may be aspirated out of the eye. The diseased lens, once removed, is replaced by an IOL.

In the natural lens, distance and near vision is provided by a mechanism known as accommodation. The natural lens is contained within the capsular bag and is soft early in life. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus alternatively on near and far objects.

As the lens ages, it becomes harder and is less able to change its shape in reaction to the tightening of the ciliary muscle. Furthermore, the ciliary muscle loses flexibility and range of motion. This makes it harder for the lens to focus on near objects, a medical condition known as presbyopia. Presbyopia affects nearly all adults upon reaching the age of 45 to 50. Various accommodative intraocular lenses (IOLs) have been proposed. However, due to limited residual accommodative forces, the mechanical design required to effectively translate accommodative force into changes in optical power has proved challenging.

SUMMARY OF THE INVENTION

Various embodiments of the present invention provide sensors for assessing residual accommodative function. In a particular embodiment, An accommodating intraocular lens includes an optic and four haptics. the optic includes an outer wall, a solid posterior optic, an anterior fluid chamber, an anterior membrane and a fluid reservoir within the outer wall surrounding the anterior fluid chamber and the solid posterior optics. The four haptics are attached to the outer wall at four attachment points. Each of the four haptics includes an arc member extending between successive attachment points and contacting the outer wall only at the attachment points. Each of the arc members is configured to compress laterally under accommodative forces. The embodiments discussed below are exemplary, and various changes can be made to these illustrative embodiments without deviating from the scope of the invention. For example, the features of one embodiment can be combined with those of another embodiment.

DETAILED DESCRIPTION

Figure 1:
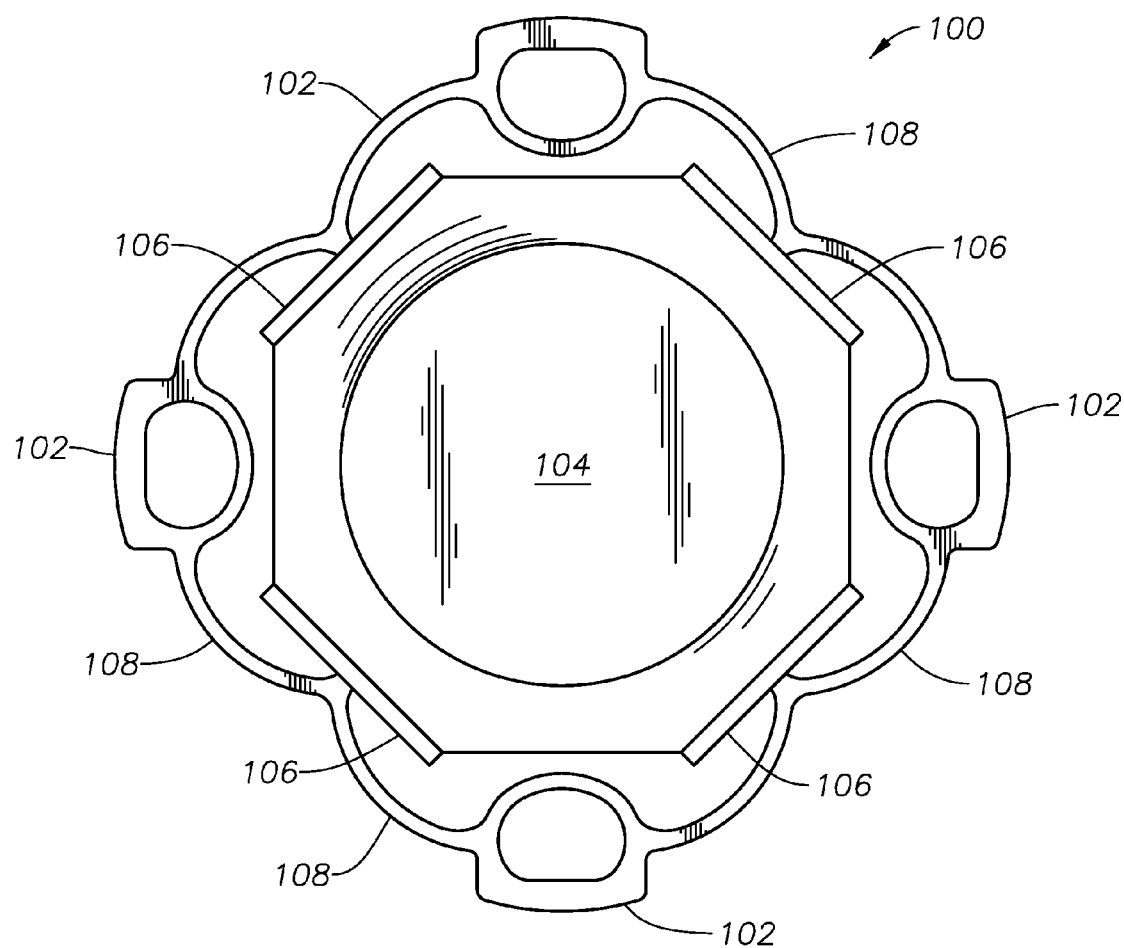
FIG. 1 illustrates an accommodating intraocular lens according to an embodiment of the invention.

As shown in FIG. 1, an accommodating intraocular lens 100 includes four haptics 102 producing uniform lateral translation around an optic 104. The haptics 102 are connected to an outer wall 202 of the optic 104 at four attachment points 106 with arc members 108 extending between the attachment points 106 to produce lateral force at each attachment point 106. The arc members 108 allow flexion in the haptics so that the lateral accommodative force is translated gradually and uniformly into force on the optics. In order to further increase the uniformity of the contact at the attachment points 106, the optics 104 has octagonal sides with four of the octagonal sides forming flat planes at the attachment points 106.

Figure 2:
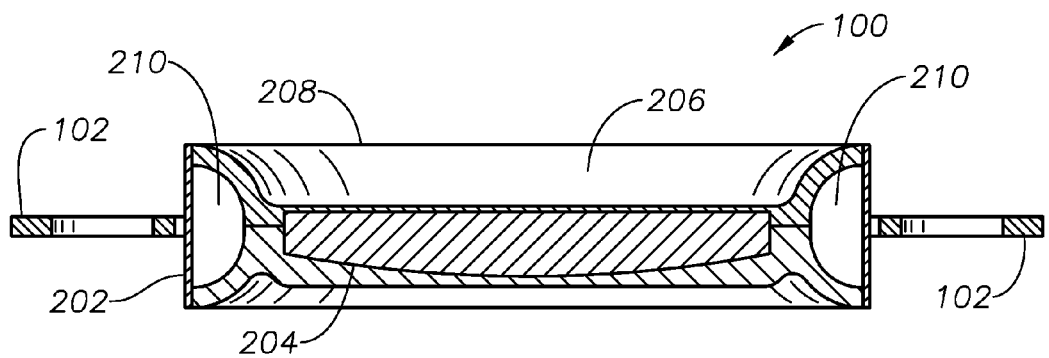
FIG. 2 illustrates a cross-sectional side view of the lens of FIG. 1.

FIG. 2 illustrates a cross-section of the lens 100, which illustrates the force-transfer mechanism for converting the lateral force into a change in optical power. The outer wall 202 of the optic 104 is attached to a solid posterior optic 204 and an anterior fluid chamber 206 covered by a membrane 208. The posterior optic 204 is plano-convex, so that when the membrane 208 of the anterior plane bulges outwardly, the optical power of the lens 100 is increased. A fluid reservoir 210 within the outer wall 202 surrounds the solid posterior optic 204 and the anterior fluid chamber 206. The fluid reservoir 206 can deform the anterior fluid chamber by pressure transfer in the depicted embodiment or, in alternative embodiments, by transferring fluid to the anterior chamber 206 via channels, such as holes or slots (not shown). As the outer side 202 is laterally compressed by the haptics 102, the fluid in the anterior chamber 206 causes the membrane 208 to bulge outwardly. This in turn produces an increase in optical power.

Those having ordinary skill in the art will appreciate that various changes can be made to the above embodiments without departing from the scope of the invention.

What is claimed is:

1. An accommodating intraocular lens, comprising:
   an optic comprising an outer wall, a solid posterior optic, an anterior fluid chamber, an anterior membrane and a fluid reservoir within the outer wall surrounding the anterior fluid chamber and the solid posterior optic; and
   four haptics each attached to the outer wall at two attachment points, each of the four haptics comprising an arc member extending between the two attachment points and contacting the outer wall only at the two attachment points, each arc member configured to compress laterally under accommodative forces.

2. The lens of claim 1, wherein the outer wall of the optic is octagonal and comprises eight planar surfaces, the two attachment points for each of the four haptics connecting to different ones of the eight planar surfaces.

3. The lens of claim 1, wherein the solid posterior optic is plano-convex.

4. The lens of claim 1, wherein the fluid reservoir and the anterior fluid chamber are connected by at least one fluid channel.

* * * * *